United States Patent
Mitchell et al.

(10) Patent No.: US 7,214,229 B2
(45) Date of Patent: May 8, 2007

(54) RADIALLY EXPANDING STENTS

(75) Inventors: Michael Mitchell, Chestnut Hill, MA (US); Mark Manasas, Dedham, MA (US); Gloria Ro Kolb, Quincy, MA (US)

(73) Assignee: Fossa Medical, Inc., Boston, MA (US)

( * ) Notice: Subject to any disclaimer, the term of this patent is extended or adjusted under 35 U.S.C. 154(b) by 0 days.

(21) Appl. No.: 10/179,902

(22) Filed: Jun. 25, 2002

(65) Prior Publication Data

US 2003/0040754 A1 Feb. 27, 2003

Related U.S. Application Data

(63) Continuation-in-part of application No. 09/755,487, filed on Jan. 5, 2001, now Pat. No. 6,709,465, which is a continuation-in-part of application No. 09/272,660, filed on Mar. 18, 1999, now Pat. No. 6,214,037.

(51) Int. Cl.
*A61F 2/04* (2006.01)
*A61B 17/22* (2006.01)

(52) U.S. Cl. .................. 606/127; 623/1.22; 623/23.69

(58) Field of Classification Search ............... 623/1.16, 623/1.22, 1.3, 1.31, 23.64–23.66, 23.69, 623/23.7; 606/127, 159, 200, 106–114, 170–180, 606/198

See application file for complete search history.

(56) References Cited

U.S. PATENT DOCUMENTS

| | | | | |
|---|---|---|---|---|
| 894,198 A | * | 7/1908 | Funk | 606/106 |
| 3,108,593 A | | 10/1963 | Glassman | 128/328 |
| 3,108,594 A | | 10/1963 | Glassman | 128/328 |
| 4,531,933 A | | 7/1985 | Norton et al. | 604/8 |
| 4,874,360 A | | 10/1989 | Goldberg et al. | 604/8 |
| 4,950,227 A | | 8/1990 | Savin et al. | 604/8 |
| 4,973,301 A | | 11/1990 | Nissenkorn | 604/8 |
| 5,129,910 A | | 7/1992 | Phan et al. | 606/127 |
| 5,246,445 A | | 9/1993 | Yachia et al. | 606/108 |
| 5,380,270 A | | 1/1995 | Ahmadzadeh | 604/9 |
| 5,380,335 A | | 1/1995 | Dormia | 606/127 |
| 5,401,257 A | | 3/1995 | Chevalier, Jr. et al. | 604/265 |
| 5,454,365 A | | 10/1995 | Bonutti | 600/204 |
| 5,496,277 A | | 3/1996 | Termin et al. | 604/104 |
| 5,496,311 A | | 3/1996 | Abele et al. | 606/28 |
| 5,496,330 A | | 3/1996 | Bates et al. | 606/127 |
| 5,518,498 A | | 5/1996 | Lindenberg et al. | 600/30 |

(Continued)

OTHER PUBLICATIONS

International Searh Report, PCT Application Serial No. PCT/US01/24409.

*Primary Examiner*—Corrine McDermott
*Assistant Examiner*—Cheryl Miller
(74) *Attorney, Agent, or Firm*—Scott E. Kamholz; Foley Hoag LLP

(57) ABSTRACT

The present disclosure is directed to embodiments of devices for capturing obstructions within passageways. The devices disclosed herein may include a flexible tubular body forming multiple flexible members arranged in a helical pattern. These flexible members may be expandable to form one or more cages when the tubular body is expanded to an increased diameter state. The cages may be generally centered around the longitudinal axis of the tubular body between the two ends of the body. Also disclosed herein are methods for capturing obstructions within passageways, methods for obtaining tissue samples from body passages, and methods for making devices for capturing obstructions within passageways.

90 Claims, 8 Drawing Sheets

U.S. PATENT DOCUMENTS

| | | |
|---|---|---|
| 5,535,756 A | 7/1996 | Parasher .................... 128/756 |
| 5,536,248 A | 7/1996 | Weaver et al. ................ 604/54 |
| 5,545,210 A | 8/1996 | Hess et al. ..................... 623/1 |
| 5,545,214 A | 8/1996 | Stevens ......................... 623/2 |
| 5,547,469 A | 8/1996 | Rowland et al. .............. 604/22 |
| 5,551,954 A | 9/1996 | Buscemi et al. ................ 623/1 |
| 5,556,413 A * | 9/1996 | Lam ............................ 623/1.2 |
| 5,575,815 A | 11/1996 | Slepian et al. .................. 623/1 |
| 5,578,018 A | 11/1996 | Rowland et al. ............ 604/280 |
| 5,593,442 A | 1/1997 | Klein ............................ 623/12 |
| 5,599,291 A | 2/1997 | Balbierz et al. ................ 604/8 |
| 5,599,299 A | 2/1997 | Weaver et al. ................ 604/54 |
| 5,599,300 A | 2/1997 | Weaver et al. ................ 604/54 |
| 5,603,694 A | 2/1997 | Brown et al. .................. 604/49 |
| 5,607,445 A | 3/1997 | Summers .................... 606/198 |
| 5,613,980 A | 3/1997 | Chauhan .................... 606/194 |
| 5,630,840 A | 5/1997 | Mayer ............................ 623/1 |
| 5,643,199 A | 7/1997 | Rowland et al. .............. 604/22 |
| 5,647,843 A | 7/1997 | Mesrobian et al. ............. 604/8 |
| 5,658,296 A | 8/1997 | Bates et al. .................. 606/127 |
| 5,665,103 A | 9/1997 | Lafontaine et al. .......... 606/192 |
| 5,681,274 A | 10/1997 | Perkins et al. .................. 604/8 |
| 5,683,362 A | 11/1997 | Rowland et al. .............. 604/96 |
| 5,700,269 A | 12/1997 | Pinchuk et al. ............. 606/108 |
| 5,713,907 A | 2/1998 | Hogendijk et al. .......... 606/108 |
| 5,733,326 A | 3/1998 | Tomonto et al. ................ 623/1 |
| 5,738,109 A | 4/1998 | Parasher .................... 128/756 |
| 5,746,745 A | 5/1998 | Abele et al. ................. 606/108 |
| 5,749,918 A | 5/1998 | Hogendijk et al. ............. 623/1 |
| 5,749,919 A * | 5/1998 | Blanc ........................ 623/1.22 |
| 5,749,921 A | 5/1998 | Lenker et al. ................... 623/1 |
| 5,755,781 A | 5/1998 | Jayaraman ...................... 623/1 |
| 5,765,682 A | 6/1998 | Bley et al. ................... 206/363 |
| 5,769,882 A | 6/1998 | Fogarty et al. .................. 623/1 |
| 5,776,142 A | 7/1998 | Gunderson .................. 606/108 |
| 5,776,162 A | 7/1998 | Kleshinski .................. 606/198 |
| 5,782,838 A | 7/1998 | Beyar et al. ................. 606/108 |
| 5,786,344 A | 7/1998 | Ratain et al. ................. 514/100 |
| 5,788,681 A | 8/1998 | Weaver et al. .............. 604/280 |
| 5,788,710 A | 8/1998 | Bates et al. .................. 606/127 |
| 5,792,145 A | 8/1998 | Bates et al. .................. 606/127 |
| 5,795,319 A | 8/1998 | Ali ................................... 604/8 |
| 5,797,952 A | 8/1998 | Klein .......................... 606/198 |
| 5,810,838 A | 9/1998 | Solar .......................... 606/108 |
| 5,814,006 A | 9/1998 | Planz ............................. 604/8 |
| 5,817,152 A | 10/1998 | Birdsall et al. .................. 623/1 |
| 5,824,037 A | 10/1998 | Fogarty et al. .................. 623/1 |
| 5,824,041 A | 10/1998 | Lenker et al. ................... 623/1 |
| 5,824,045 A | 10/1998 | Alt .................................. 623/1 |
| 5,830,217 A | 11/1998 | Ryan .......................... 606/108 |
| 5,843,028 A | 12/1998 | Weaver et al. ................ 604/54 |
| 5,843,156 A | 12/1998 | Slepian et al. .................. 623/1 |
| 5,868,698 A | 2/1999 | Rowland et al. .............. 604/22 |
| 5,868,783 A | 2/1999 | Tower ........................ 606/198 |
| 5,873,907 A | 2/1999 | Frantzen ........................ 623/1 |
| 5,879,713 A | 3/1999 | Roth et al. ................... 424/489 |
| 5,885,258 A | 3/1999 | Sachdeva et al. ............ 604/281 |
| 5,897,533 A | 4/1999 | Glickman ................... 604/256 |
| 5,902,284 A | 5/1999 | Suzuki et al. ................ 604/265 |
| 5,902,332 A | 5/1999 | Schatz ............................ 623/1 |
| 5,908,435 A | 6/1999 | Samuels ...................... 606/200 |
| 5,911,732 A | 6/1999 | Hojeibane .................. 606/194 |
| 5,911,733 A | 6/1999 | Parodi ........................ 606/198 |
| 5,914,345 A | 6/1999 | Slepian et al. ............. 514/496 |
| 5,921,952 A | 7/1999 | Demond, III et al. ........... 604/8 |
| 5,928,280 A | 7/1999 | Hansen et al. .................. 623/1 |
| 5,938,585 A | 8/1999 | Donofrio .................... 600/115 |
| 5,944,728 A | 8/1999 | Bates .......................... 606/194 |
| 5,957,932 A | 9/1999 | Bates et al. .................. 606/127 |
| 5,961,536 A | 10/1999 | Mickley et al. ............. 606/194 |
| 5,968,068 A | 10/1999 | Dehdashtian et al. ....... 606/192 |
| 5,968,088 A | 10/1999 | Hansen et al. .................. 623/1 |
| 5,968,091 A | 10/1999 | Pinchuk et al. ................. 623/1 |
| 5,971,992 A | 10/1999 | Solar .......................... 606/108 |
| 5,984,963 A | 11/1999 | Ryan et al. .................... 623/12 |
| 5,989,266 A | 11/1999 | Foster ........................ 606/127 |
| 6,004,328 A | 12/1999 | Solar .......................... 606/108 |
| 6,019,779 A * | 2/2000 | Thorud et al. .............. 606/198 |
| 6,027,528 A | 2/2000 | Tomonto et al. ................ 623/1 |
| 6,042,553 A | 3/2000 | Solar et al. .................. 600/585 |
| 6,066,167 A | 5/2000 | Lau et al. ........................ 623/1 |
| 6,066,168 A | 5/2000 | Lau et al. .................... 623/1.16 |
| 6,071,956 A | 6/2000 | Slepian et al. .............. 514/496 |
| 6,080,191 A | 6/2000 | Summers ................... 623/1.22 |
| 6,099,534 A | 8/2000 | Bates et al. .................. 606/127 |
| 6,110,191 A | 8/2000 | Dehdashtian et al. ....... 606/192 |
| 6,110,198 A | 8/2000 | Fogarty et al. ............. 623/1.12 |
| 6,117,104 A | 9/2000 | Fitz .......................... 604/96.01 |
| 6,120,534 A | 9/2000 | Ruiz .......................... 623/1.19 |
| 6,123,722 A | 9/2000 | Fogarty et al. .............. 623/1.1 |
| 6,124,007 A | 9/2000 | Wang et al. ................ 428/35.2 |
| 6,126,685 A | 10/2000 | Lenker et al. .................. 623/1 |
| 6,129,761 A | 10/2000 | Hubbell ........................ 623/11 |
| 6,133,242 A | 10/2000 | Zalewski et al. ............. 514/44 |
| 6,143,014 A | 11/2000 | Dehdashtian et al. ....... 606/192 |
| 6,156,064 A | 12/2000 | Chouinard ................. 623/1.44 |
| 6,159,220 A | 12/2000 | Gobron et al. .............. 606/127 |
| 6,159,230 A | 12/2000 | Samuels ...................... 606/200 |
| 6,165,209 A | 12/2000 | Patterson et al. ............ 623/1.1 |
| 6,168,571 B1 | 1/2001 | Solar et al. .................. 600/585 |
| 6,168,603 B1 | 1/2001 | Leslie et al. ................ 606/114 |
| 6,171,338 B1 | 1/2001 | Talja et al. ................. 623/1.22 |
| 6,183,482 B1 | 2/2001 | Bates et al. .................. 606/127 |
| 6,193,745 B1 | 2/2001 | Fogarty et al. ............. 623/1.12 |
| 6,197,047 B1 | 3/2001 | Kranz ........................ 623/1.15 |
| 6,200,307 B1 | 3/2001 | Kasinkas et al. ............... 606/7 |
| 6,210,393 B1 | 4/2001 | Brisken ...................... 604/508 |
| 6,221,042 B1 | 4/2001 | Adams ...................... 604/96.01 |
| 6,224,612 B1 | 5/2001 | Bates et al. .................. 606/114 |
| 6,241,719 B1 | 6/2001 | Wallace et al. ............. 604/509 |
| 6,248,100 B1 | 6/2001 | de Toledo et al. .......... 604/540 |
| 6,254,571 B1 | 7/2001 | Hart ............................ 604/107 |
| 6,254,608 B1 | 7/2001 | Solar .......................... 606/108 |
| 6,258,118 B1 | 7/2001 | Baum et al. ................ 623/1.19 |
| 6,264,624 B1 | 7/2001 | Desmond, III et al. ......... 604/8 |
| 6,264,664 B1 | 7/2001 | Avellanet ................... 606/128 |
| 6,267,775 B1 | 7/2001 | Clerc et al. ................. 606/198 |
| 6,273,895 B1 | 8/2001 | Pinchuk et al. ............. 606/108 |
| 6,277,065 B1 | 8/2001 | Donofrio .................... 600/115 |
| 6,290,718 B1 | 9/2001 | Grooms et al. ................. 623/1 |
| 6,290,729 B1 | 9/2001 | Slepian et al. ............ 623/23.72 |
| 6,295,940 B1 | 10/2001 | Shonteff ........................ 112/63 |
| 6,302,895 B1 | 10/2001 | Gobron et al. .............. 606/127 |
| 6,306,166 B1 | 10/2001 | Barry et al. ................. 623/1.46 |
| 6,306,426 B1 | 10/2001 | Olejnik et al. ............... 424/426 |
| 6,309,411 B1 | 10/2001 | Lashinski et al. ............ 623/1.1 |
| 6,312,463 B1 | 11/2001 | Rourke et al. ............. 623/1.39 |
| 6,319,261 B1 | 11/2001 | Bowers ...................... 606/127 |
| 6,319,262 B1 | 11/2001 | Bates et al. .................. 606/127 |
| 6,323,184 B1 | 11/2001 | Zalewski et al. ............. 514/44 |
| 6,325,825 B1 | 12/2001 | Kula et al. .................... 623/1.3 |
| 6,344,055 B1 | 2/2002 | Shukov ...................... 623/1.15 |
| 6,395,021 B1 | 5/2002 | Hart et al. ................... 623/1.15 |
| 6,500,182 B2 * | 12/2002 | Foster ........................ 606/127 |
| 6,569,183 B1 * | 5/2003 | Kim et al. ................... 606/200 |
| 6,652,548 B2 * | 11/2003 | Evans et al. ................. 606/159 |
| 2001/0041899 A1 | 11/2001 | Foster ........................ 606/127 |
| 2002/0183853 A1 | 12/2002 | Mitchell et al. ............. 623/23.7 |
| 2002/0193828 A1 * | 12/2002 | Griffin et al. |
| 2003/0097172 A1 | 5/2003 | Shalev et al. .............. 623/1.31 |
| 2003/0135268 A1 | 7/2003 | Desai ......................... 623/1.19 |

* cited by examiner

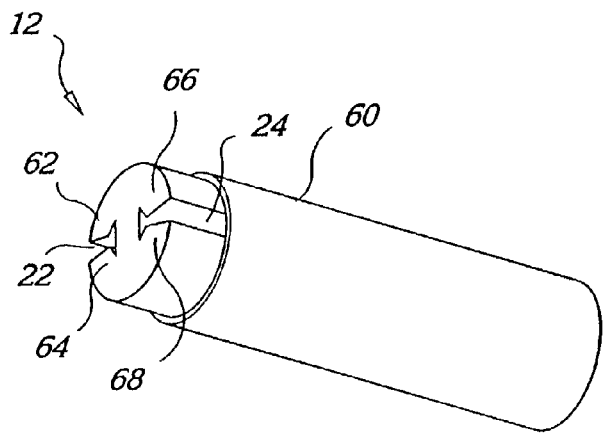
FIG. 10
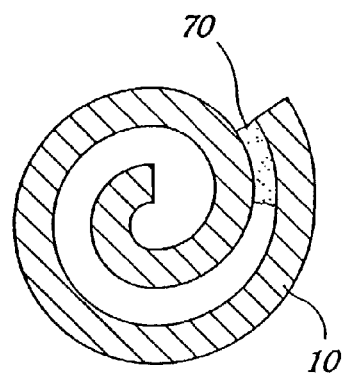
FIG. 11
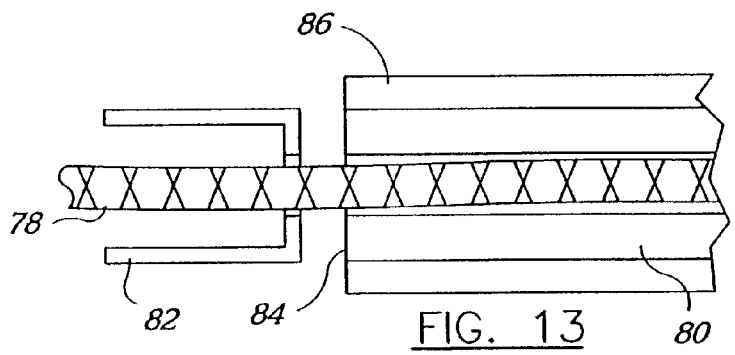
FIG. 13
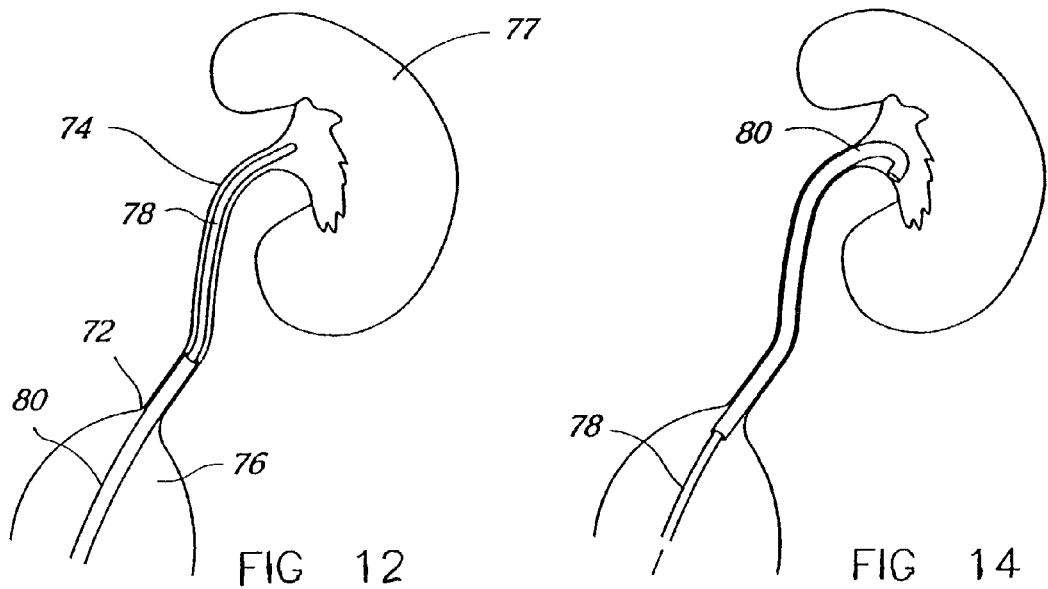
FIG 12
FIG 14

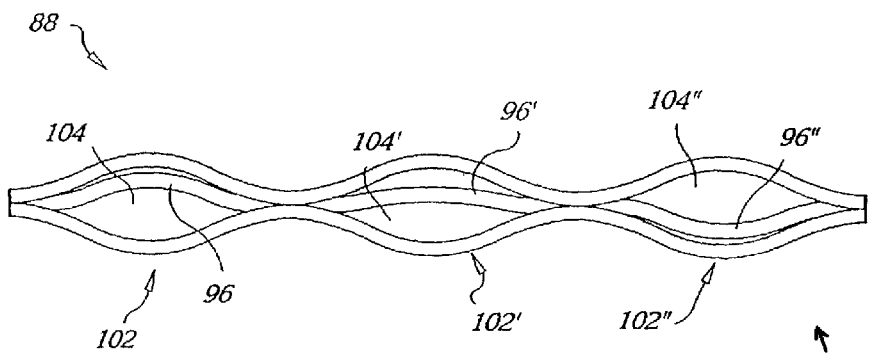
FIG. 19
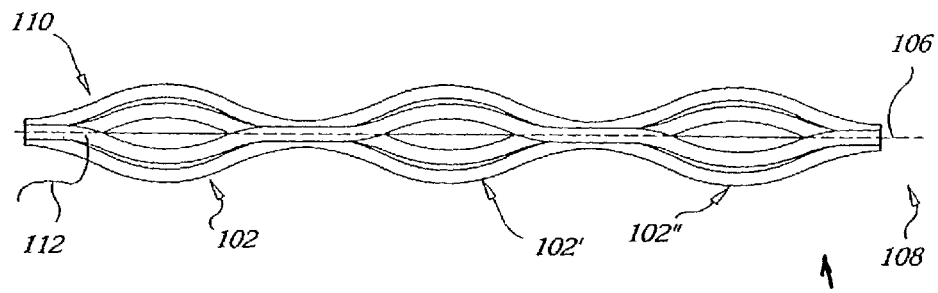
FIG. 20
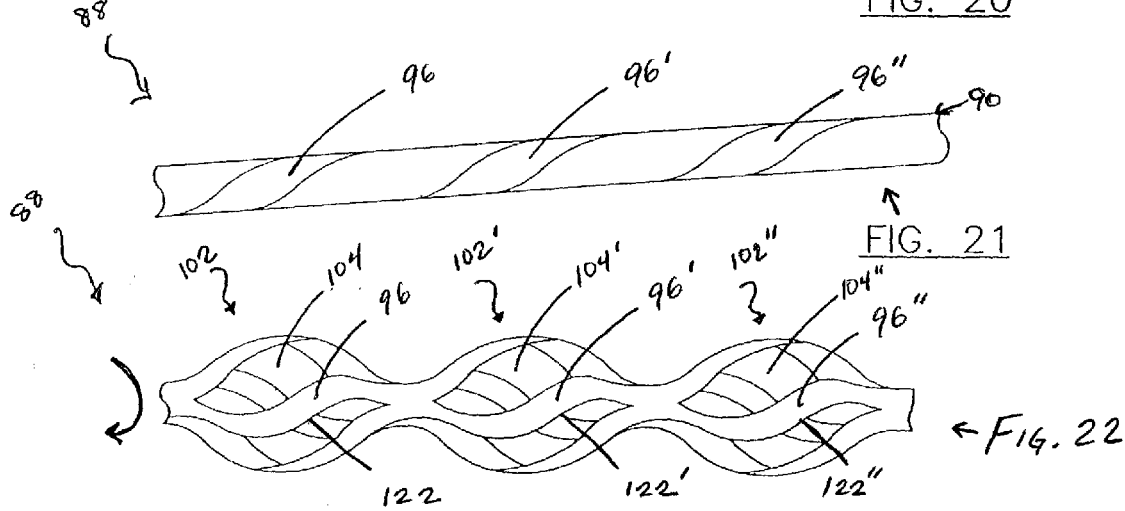
FIG. 21
FIG. 22

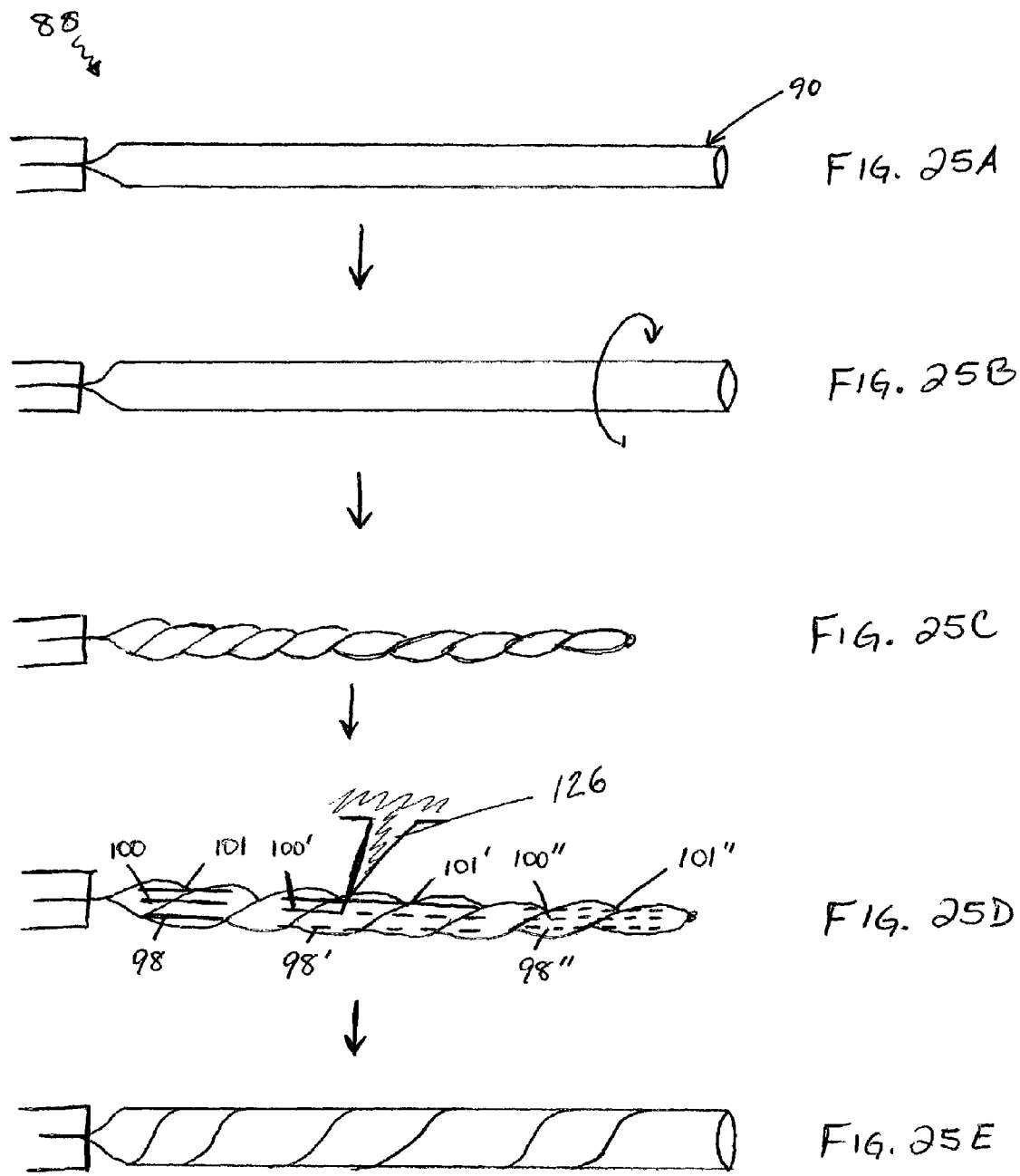

RADIALLY EXPANDING STENTS

CROSS-REFERENCE TO RELATED APPLICATIONS

The present application is a continuation-in-part of U.S. application Ser. No. 09/755,487, filed Jan. 5, 2001, now U.S. Pat. No. 6,709,465, which is a continuation-in-part of U.S. application Ser. No. 09/272,660, filed Mar. 18, 1999, now U.S. Pat. No. 6,214,037. Each of the above-referenced patents and pending applications is incorporated herein by reference.

BACKGROUND

Treatment of obstructions within passageways is a common challenge faced by medical professionals. These obstructions can occur within body passages such as the ureter, pancreaticobiliary ducts, bowel passages, and airways, or within tubing connected to patients such as external drainage tubing, feeding tubes, intravenous tubes, or chest tubes. Removing these obstructions in a simple and cost effective manner, as well as in a manner involving the least amount of discomfort for the patient as possible, is a goal shared by medical practitioners and medical product manufacturers alike.

In one typical example, calculus or stones in the urinary tract or kidneys arise because of the breakdown of a delicate balance in the body. Specifically, the kidneys must conserve water to function, but they must excrete materials that have a low solubility. These opposing requirements must be balanced during adaptation to diet, climate and activity. The problem is mitigated to some degree because urine contains substances that inhibit crystallization of stone forming minerals. However, when urine becomes supersaturated with insoluble materials, because excretion rates are excessive and/or because water conservation is extreme, crystals form and may grow and aggregate to form a stone.

Although small crystals are readily voided from the kidney with urine, the larger stones may become dislodged from the kidney and enter the ureter or occlude the uretero-pelvic or uretero-vesical junction, causing pain and obstruction. Although some stones can ultimately traverse the ureter, their passage may produce pain and bleeding. The pain can be so severe that narcotic drugs are needed for its control.

Removal of stones from the kidneys or urinary tract can be effected medically or surgically. A well known surgical approach involves passing a flexible basket in a retrograde manner up the ureter from the bladder, and using the basket to capture the stones. Another surgical technique, known as extracorporeal lithotripsy, entails transmission of high-intensity shock waves from outside the body to fragment the stones within the body. The resulting stone fragments are then voided with urine. Yet another surgical technique, percutaneous ultrasonic lithotripsy, requires the passage of a rigid cystoscopy-like instrument in the renal pelvis through a small incision in the flank whereupon stones are broken up by a small ultrasound transducer and removed directly. Another surgical technique is laser lithotripsy via a ureteroscope. All of these procedures, which can be quite painful, are elaborate and expensive, and do not always result in complete removal of the stones and fragments.

Stents are used to decompress ureteral obstruction, ensuring that urine drains from the kidney to the bladder. It has also been recognized that placement of a stent within the ureter can help small stones and stone fragments to transit the ureter. In a typical procedure involving a stent, a guide wire is passed through the ureter to the renal pelvis. A hollow, flexible, cylindrical stent is then advanced with a pusher over the guide wire. The guide wire and pusher are then extracted from the stent and the body, leaving an open lumen for urine to pass through. However, because the lumen defined by the cylindrical stent is even smaller than the ureter itself, all but the smallest stones and sludge are precluded from passing therethrough. Some fragments are able to pass around the ureteral stent but larger stone fragments are unable to pass.

SUMMARY

The present disclosure is directed to embodiments of stents and associated methods for capturing obstructions from a variety of passageways as well as methods for manufacturing such stents. The stents disclosed herein are designed for decompressing an obstructed passageway and facilitating the capture of the obstructions within the passageway. Once captured, the obstructions may be reduced within the passageway while being held by the stent or, alternatively, may be extracted from the passageway. Additionally, certain exemplary embodiments of the stents disclosed herein may be utilized to obtain tissue samples from body passages.

In accordance with one exemplary embodiment, a stent for capturing an obstruction within a passageway includes a flexible tubular body having a proximal end and a distal end. The flexible tubular body comprises a plurality of flexible elongate members helically oriented relative to the longitudinal axis of the tubular body. The flexible elongate members are expandable to form one or more cages that are movable from a contracted state to an increased diameter state. The cages are centered about the longitudinal axis of the flexible tubular body between the proximal end and the distal end of the stent.

In accordance with another exemplary embodiment, a method for capturing an obstruction within a passageway includes guiding a stent through a passageway, the stent having a flexible tubular body comprising a plurality of flexible members oriented at an angle greater than 0° relative to the longitudinal axis of the tubular body. Once the tubular body has reached a desired location within the passageway, the tubular body is twisted to expand the flexible members and create one or more cages. Either during expansion or once expanded, the cages may capture an obstruction within one or more of the cages.

In accordance with another exemplary embodiment, a method for capturing an obstruction within a passageway includes guiding a stent through a passageway, the stent having a flexible tubular body comprising a plurality of flexible members oriented at an angle greater than 0° relative to the longitudinal axis of the tubular body. Once the tubular body has reached a desired location within the passageway, the tubular body is twisted to expand the flexible members and create one or more cages. Either during expansion or once expanded, the cages may capture an obstruction within one or more of the cages. After capturing one or more obstructions, the tubular body is rotated in a direction consistent with the original twisting to displace the captured obstructions through the tubular body in a direction away from the distal end of the tubular body in a corkscrew fashion.

In accordance with one exemplary embodiment, a method for making a stent includes securing one end of a flexible tubular body and then twisting the body about the longitudinal axis of the body. While twisted, multiple longitudinal apertures are created in the flexible tubular body. These apertures penetrate the body wall of the tubular body and define multiple flexible elongate members in the body wall. Subsequently, the tubular body is released creating a flexible tubular body with helical apertures defining multiple flexible members arranged in a helical pattern.

In accordance with another exemplary embodiment, a method for obtaining tissue samples from a body passage includes guiding a stent through a passageway, the stent having a flexible tubular body comprising a plurality of flexible members oriented at an angle greater than 0° relative to the longitudinal axis of the tubular body. The flexible members of this stent have at least one abrading edge. Once the tubular body has reached a desired location within the body passage, the tubular body is twisted to expand the flexible members and create one or more cages. During expansion and while expanded, the tubular body may be rotated in the same direction as the original twisting to bring the abrading edge into contact with an inner surface of the body passage and to scrape a tissue sample from the inner surface of the body passage. The tubular body may then be twisted in the opposite direction to contract the stent and capture the tissue samples within the cages prior to removing the device from the body passage.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIG. 10 illustrates the stent of FIG. 3 compressed within a sleeve;

FIG. 11 shows the stent of FIG. 7 held in a compressed state with an adhesive;

FIG. 12 depicts a step in a procedure for placing a stent in accordance with the invention;

FIG. 13 illustrates the stent and associated components;

FIG. 14 shows removal of a guidewire from the stent;

FIG. 19 is a perspective view of the stent of FIG. 18, shown in an expanded state;

FIG. 20 is a perspective view of a stent in accordance with the present invention, shown in an expanded state;

FIG. 21 is a perspective view of a stent in accordance with the present invention, shown in a contracted state;

FIG. 22 is a perspective view of the stent of FIG. 21, shown in an expanded state;

FIGS. 25A–25E illustrate a method of making the stent of FIG. 21 and FIG. 22 in accordance with the present invention.

DETAILED DESCRIPTION OF EXEMPLARY EMBODIMENTS

Figure 1:
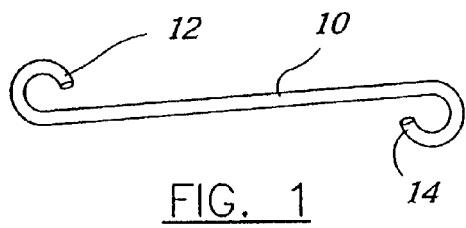
FIG. 1 is a perspective view of a stent in accordance with the present invention.

FIG. 1 is a perspective view of a stent in accordance with the invention. The stent includes a body 10 having a first end portion 12 and a second end portion 14. The stent body and end portions are flexible enough to assume a substantially linear configuration. However, in a static state, the end portions of the stent can assume a curved orientation as shown. Details regarding the features, exemplary dimensions, and use of the stent follow.

Figure 2:
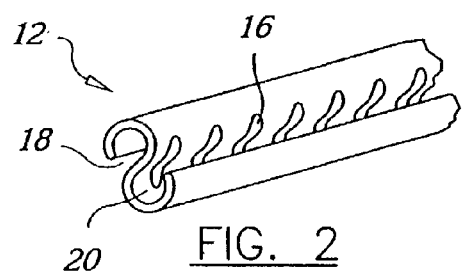
FIGS. 2–9D are detailed views of end portions of stents in accordance with present invention.

FIG. 2 is a detailed view of a straightened first end portion 12 of an exemplary stent. The opposite, second end portion 14 (not shown in FIGS. 2–8) is substantially identical to the first end portion. In this view, the stent body and end portions have an "S" shaped cross-section. Apertures 16 are provided along all or a portion of the length of the stent. Although the apertures 16 are shown as being elongate, they can also be oval or circular. The "S" shape of the stent body and end portions defines two longitudinal channels 18 and 20. As used herein, a channel is a path defined, or at least partially bound, by a portion of the stent body or end portions.

Figure 3:
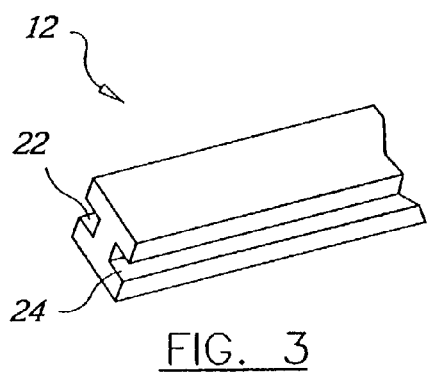

FIG. 3 illustrates the stent in an "I" configuration. Although not illustrated other than FIG. 2, apertures can be provided in this and all other stent configurations. The "I" shape defines two longitudinal channels 22 and 24.

Figure 4:
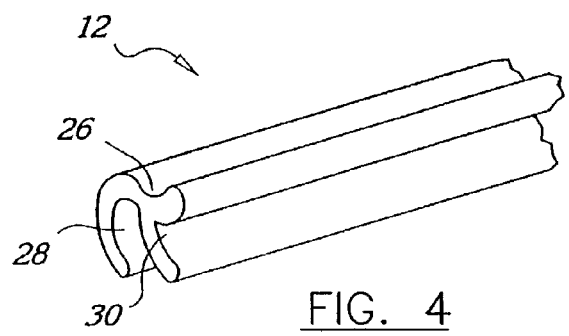

FIG. 4 illustrates the stent configured to provide three channels 26, 28 and 30.

Figure 5:
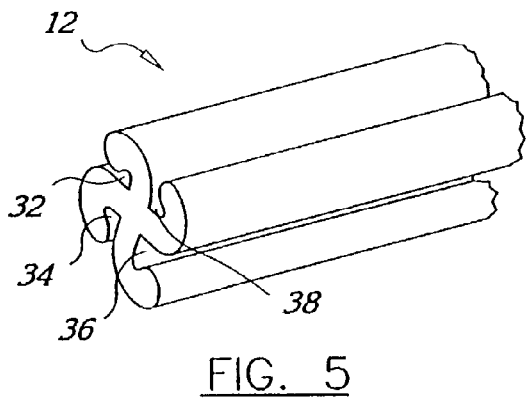

FIG. 5 illustrates the stent configured to provide four channels 32, 34, 36 and 38.

Figure 6:
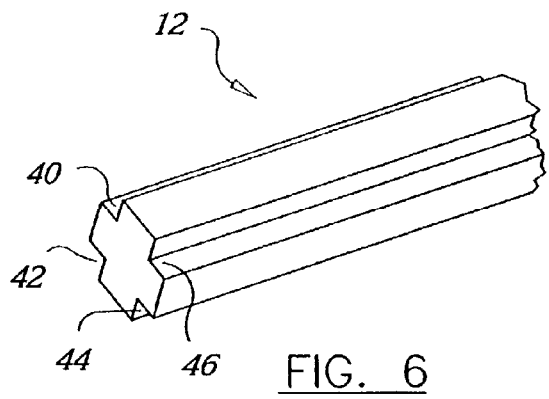

FIG. 6 also depicts the stent that defines four channels 40, 42, 44 and 46.

Figure 7:
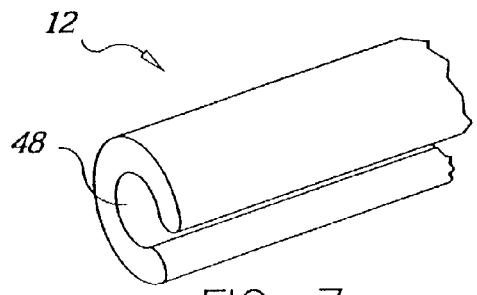

FIG. 7 depicts a stent with a single channel 48.

Figure 8:
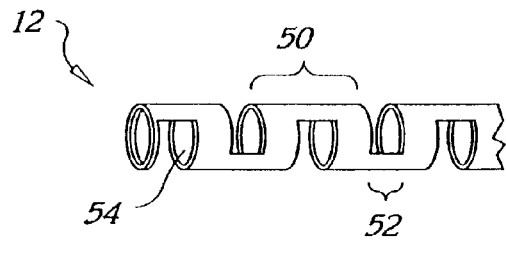

FIG. 8 illustrates a stent having segments 50 joined by linking regions 52 and defining a channel 54. In one embodiment, the linking regions bias or urge adjacent segments away from coaxial alignment. Thus, the channel(s) need not be linear and can be somewhat discontinuous or multiple channels are provided.

Figure 9A:
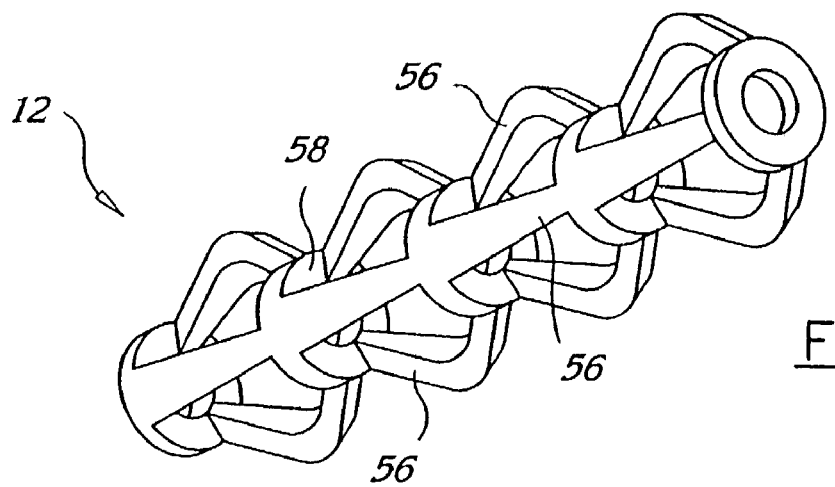
Figure 9B:
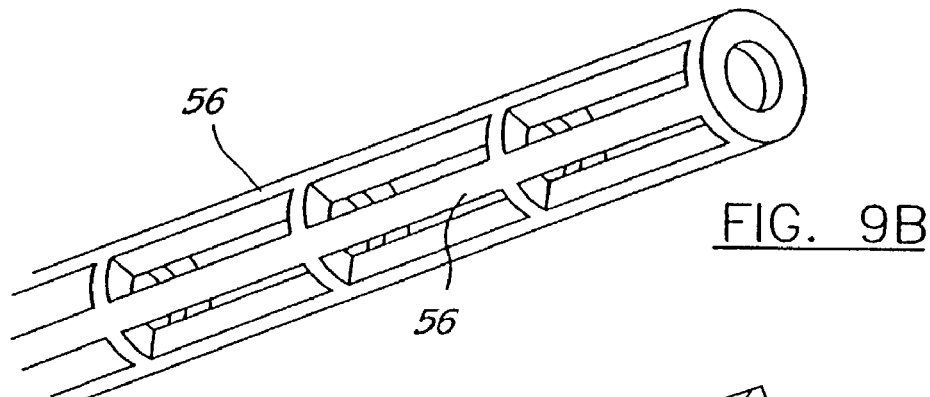
Figure 9C:
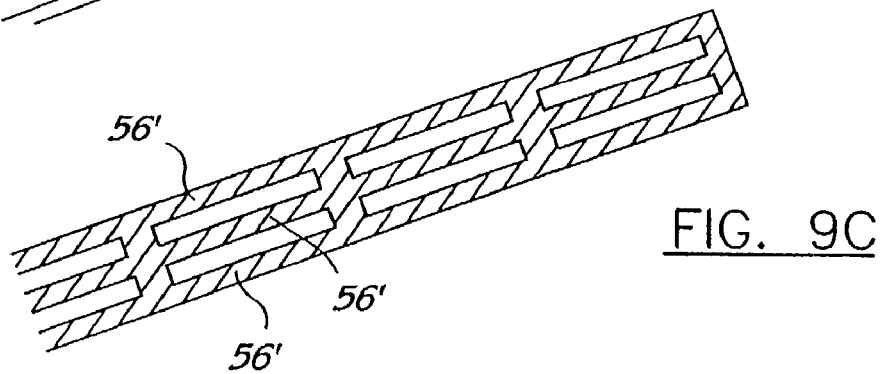
Figure 9D:
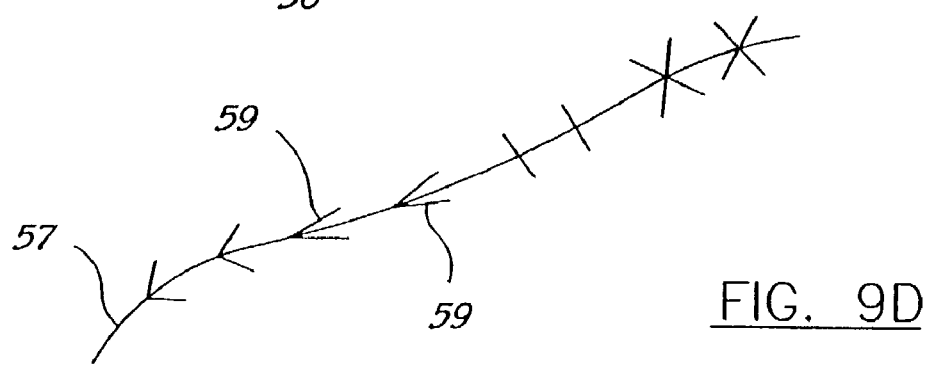

FIG. 9A illustrates a stent having resilient, substantially-longitudinal elements 56 connecting to disk-like structures 58. In the illustration, the elements 56 are bowed outward from a central axis of the stent, in a cage expanded state, to provide the stent with an undulating surface and alternating larger and smaller localized circumferential regions. FIG. 9B illustrates the stent of FIG. 9A with the elements 56 in a substantially linear or non-bowed configuration, a cage contracted state. FIG. 9C depicts yet another embodiment of the stent, wherein the stent is substantially planar in a first configuration as shown. In the cage expanded state, elements 56' bow outward as shown with respect to the stent of FIG. 9A. FIG. 9D illustrates yet another embodiment, wherein an elongate flexible body is provided with barbs 59 that can be transitioned from a reduced diameter configuration 59 to a larger diameter configuration. In the illustration, barbs 59 are shown in different configurations and states. The stents of FIGS. 9A–D can be transitioned from a uniform/reduced diameter configuration to a nonuniform/larger diameter configuration by compressing the stent longitudinally, or by removing a restraining force from outwardly biased elements 56 or 56'. In exemplary embodiments a restraining force is provided by a sleeve as shown with respect to FIG. 10 or with adhesives as described below with respect to FIG. 11.

FIG. 10 depicts the stent of FIG. 3 within a sleeve 60. Because at least a portion of the stent is flexible, such as body portions 62, 64, 66 and 68 that define the channels 22 and 24, the stent can be folded into a sleeve having a smaller diameter than the stent in its unfolded state. If the material of the stent is compressible, the stent can be placed into an even smaller diameter sleeve. The sleeve 60 thus can serve at least two important functions: it temporarily reduces the diameter of the stent and, until removal, it provides a smooth exterior surface. Both of these features facilitate deployment of the stent as described below.

Alternatively, as shown in FIG. 11, the stent in a configuration such as shown in the sectional end view of FIG. 7 can be folded or rolled and held in that configuration with a water or acid soluble adhesive 70. Thus, when the adhesive dissolves, the stent unfolds or unrolls.

Exemplary stents are made of silicone and have lengths in the range of 22 to 32 centimeters for adults and about 16 to 18 centimeters for children. However, the length of the stent can be modified as required. A stent can have a diameter of about 7.0 FR for placement within a ureteral orifice 3 millimeters in diameter. Stents as described herein are well suited for removal of a stone up to 10 millimeters in diameter.

FIG. 12 illustrates a step of an exemplary procedure, wherein a cystoscope has been used to find the orifice 72 of the ureter 74 leading between the bladder 76 and a kidney 77. A flexible guidewire 78, such as is known in the art, has been guided through the orifice 72 and into the ureter. A stent 80 in accordance with the invention is selected, placed over the wire 78, and passed into the ureter 74.

As illustrated in FIG. 13, a pusher 82 can be placed over the guidewire 78 and pressed against the proximal end 84 of the stent 80. In this illustration, the stent 80 is compressed within a sleeve 86. The pusher 82, if used, and the flexible guidewire 78 are then removed, as shown in FIG. 14, and the stent is left in place. If a sleeve is used, it can also be removed from the stent.

Figure 15:
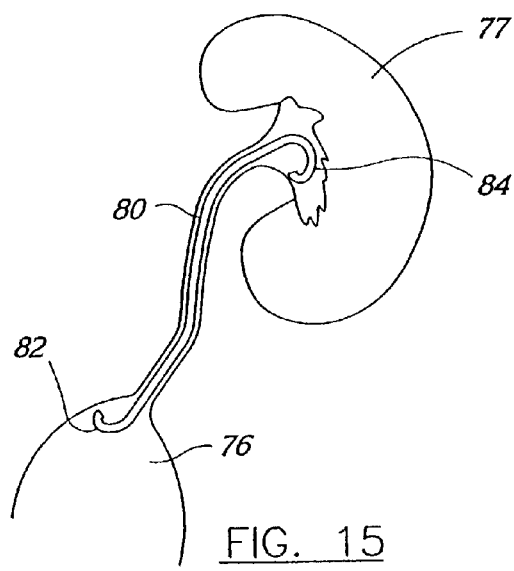
FIG. 15 illustrates the stent in position within a dilated passageway.

When the wire and sleeve are removed, the relatively unconfined ends of the stent form a retention shape, such as by curling to form a "double-J," as is known in the art, and as shown in FIG. 15. A first curled end portion (or "J") anchors a first end 82 of the stent 80 within the bladder 76 and a second curled end portion anchors a second end 84 of the stent within the kidney 77.

Figure 16:
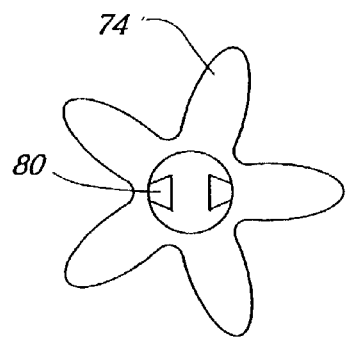
FIG. 16 illustrates the stent within an undilated passageway.
Figure 17:
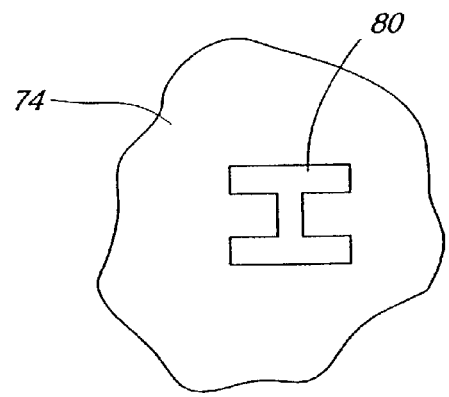
FIG. 17 illustrates the stent of FIG. 16, after the passageway has dilated.

When the stent 80 is in place, the ureter 74 dilates around the stent naturally from a normal state as shown in FIG. 16 to an increased diameter or dilated state as illustrated in FIG. 17. The effect is particularly evident when the stent selected for insertion is a radially expandable stent. Although a stone may not have been able to pass through an undilated ureter, after dilation the stone (depending on its size) is able to pass through the increased diameter ureter. After the stone(s) have been eliminated from the body, the stent is removed from the body. Any stones trapped in the channel(s) are removed with the stent. The channel(s) help to maximize a flow path for urine and they provide an enlarged path for the stones to wash into the bladder. By contrast with known cylindrical stents, the open cross-section of the present stent is not easily clogged. Furthermore, the open channel configurations do not readily become pinched closed as do known complete, cylindrical, catheter-like tubes.

Instead of removing the stent using techniques known to those skilled in the art, the stent can be fabricated from a material that degrades into small pieces or dissolves so that it can be passed with urine. The stent can be made of a urine, water, acid, or base soluble material such as sugar, polydioxanone, polyglecaprone 25, polyglactine, gelatine sponge, hylauronan-benzyl ester hyaluronic acid, or cyanoacrylate. Alternatively, the stent can dissolve when exposed to ultrasound. An exemplary stent dissolves completely within a week or two. Even if dissolution of the stent begins when the sleeve is removed, the rate of deterioration is slow enough so that the stent will perform its intended purpose.

In addition to placement in a ureter, the stent in accordance with the invention can be therapeutically effective with respect to obstruction, stricture and external compression of any tubular structure within the body including airways, bile ducts, pancreatic ducts, the bowel, blood vessels and the urethra.

Figure 18:
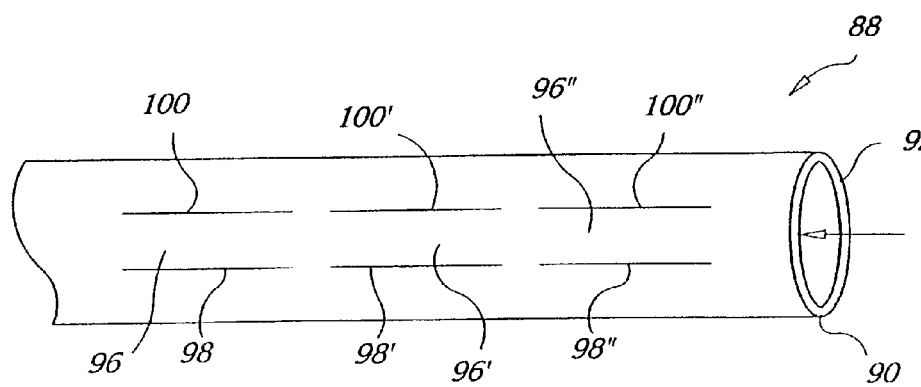
FIG. 18 is a perspective view of a stent in accordance with the present invention shown in a contracted state.

FIG. 18 is a perspective view of another embodiment of a stent similar to the device shown in FIG. 9A. The stent has a body 88 which includes a flexible tube 90, a body wall 92 with an outer surface and an inner surface that define a lumen 94. The body wall 92 has a plurality of flexible elongate members, here exemplified by representative members, 96, 96', 96". These flexible members are characterized as elongate because their length in the longitudinal direction is greater than their width in the circumferential direction. The flexible elongate members are arranged in groups of three circumferentially-spaced members. The length of the flexible elongate members can be from slightly less than the full length of the body to less than 1 mm. In some embodiments, the length of the members is from 0.1 cm to 10.0 cm and in other embodiments, the length of the members is from 1.0 cm to 5.0 cm. Further, in some embodiments the lengths of the members is from 2.0 cm to 3.0 cm. The length of the members may vary with the requirements of a given procedure or the size of an obstruction.

Along the flexible members 96, 96', 96" are apertures 98, 98', 98" and apertures 100, 100', 100", which separate flexible members from their adjacent neighboring flexible members. Although the apertures are shown as being elongate, they can also be oval, circular or may be slot-like as shown in FIG. 9. When in a contracted state, the distance between the flexible elongate members and their adjacent neighbors range from completely touching to not touching at all. Also as shown in FIG. 18, when the flexible members are in a contracted state, the body 88 has a substantially uniform diameter with a smooth exterior surface.

Turning now to FIG. 19, the stent of FIG. 18 is shown in an expanded state. When in the expanded state, the flexible elongate members 96, 96', 96" are away from each adjacent flexible elongate member thereby defining a plurality of cages 102, 102', 102" and void spaces 104, 104' and 104" along the body 88. In the expanded state, the flexible elongate members are in a spaced-apart relation with regard to adjacent flexible elongate members. While these figures show three flexible elongate members per cage, it will be readily understood that various numbers of members may be employed. For example, FIG. 20 shows a stent with four flexible elongate members per cage in an expanded state.

The cages can be transitioned from a contracted state, as shown in FIG. 18, to an expanded state, as shown in FIGS. 19 and 20. One way that this can be accomplished is by shortening the length of the body 88, for example by pushing one or both ends of the body 88 axially to shorten the distance between the two ends. Alternatively, a filament 106 can be provided that is secured to a distal region 108 of the body 88 as shown in FIG. 20, wherein pulling the filament toward the proximal end 110 of the body 88 shortens the body causing the members to bow outward and form cages 102, 102' and 102". To prevent the filament 106 from obstructing the cages, the filament can be pulled free of the distal region 108 once sufficient force has been applied to deform flexible members that define the cage.

Another way to facilitate the transition of the cages from one state to the other is to construct the cages so that they are biased to take an expanded state. The cages are then held in a contracted state by a restraining force as described in more detail above (e.g. sheaths or adhesives). Once the restraining force is removed, the cage will expand to expose the void spaces. When removal of the device is desired, the proximal end of the device or a tether secured thereto can be pulled. An exemplary tether 112 is shown in FIG. 20. In this embodiment, when the tether 112 is pulled, the device will transition from the expanded state to the contracted state. The pulling of one end of the device acts to lengthen the body, thereby contracting the cages.

When the stent is in the contracted state, it has a cage diameter that is less than a cage diameter when the device is in the expanded state. The outer diameter in the contracted state is constant and can range from 1 mm to 5 mm while the outer diameter in the expanded state is variable due to the undulating shape, with the cage outer diameter ranging from 5 mm to 20 mm. By way of example, stents for use in a ureter may have an outer diameter in a contracted state of approximately 7.0 FR (0.092"), biopsy scrapers for use in breast ducts may have outer diameters in a contracted state of approximately 1.0 FR (0.0125"), stents for use in pancreaticobiliary ducts may have outer diameters in a contracted state from 3.0 FR (0.039") to 7.0 FR (0.092"), stents for use in fallopian tubes may have outer diameters in a contracted state of approximately 14.0 FR (0.184"), tubes for use in an esophagus may have outer diameters in a contracted state of approximately 18 mm (0.71"), and biopsy scrapers for use in a colon may have outer diameters in a contracted state from 25 mm (1.0") to 35 mm (1.4"). Generally, expanded cage diameters are 4–5 times greater than the associated contracted state diameters.

FIG. 21 is a perspective view of a stent, in accordance with the invention, shown in a contracted state. In this embodiment, the flexible elongate members 96, 96', 96" are configured in a helical pattern, wherein the flexible elongate members are arranged in the form of a spiral. FIG. 22 shows the stent of FIG. 21 in an expanded state. As shown in FIG. 22, the flexible elongate members 96, 96', 96", when expanded, define three-dimensional cages 102, 102', 102". These cages are also arranged in a helical pattern. The three-dimensional cages form a helical pattern due to the underlying helical pattern of the flexible elongate members as well as the associated helical pattern of the exposed void spaces 104, 104', 104". In another embodiment, the members are linear or other shapes, but not parallel to the longitudinal axis of the body 88.

To achieve the helical pattern illustrated in FIGS. 21–22, flexible elongate members 96, 96', 96" may be oriented at an angle greater than 0° but less than 90° relative to the longitudinal axis of the device body 88. In one exemplary embodiment, the flexible elongate members may be oriented at a ±45° angle. One skilled in the art will appreciate that the stents described above can be configured for insertion into a variety of passageways, including body passages and tubing connected to subjects. For example, the stents may be made from a variety of materials such as polymers (e.g., polyurethane, polyethylene, and fiber-reinforced polyethylene), shape-memory materials (e.g., shape-memory polymers and shape-memory metal alloys such as nitinol), silicone, metals such as titanium, or bioabsorbable materials. Also, the polymeric stents may have barium added to their base materials in order to provide radiopacity and improve visualization if the base material is not inherently radiopaque. For example, in a preferred embodiment, a stent may be manufactured from a 20% barium loaded polyurethane. Additionally, the stents may be impregnated or coated with an antimicrobial or antibiotic substance, an anti-inflammatory substance to relax the passageway, a topical anesthetic substance, or a substance capable of treating an obstruction. Similarly, the stents may be coated on their surface with hydrophilic coatings, lubricious coatings such as gels or silicone, or vacuum-deposited surface coatings such as Parylene or PTFE, to facilitate insertion and removal from a passageway and a sheath. Furthermore, the stents may be marked or tagged with radiopaque or non-ferromagnetic materials to facilitate in vivo visualization via x-ray, magnetic resonance imaging or ultrasound. The stents can also be manufactured in a variety of sizes to match the requirements of the particular body passage or tubing as detailed above. Generally, stents with a diameter of 3.0 FR or greater can be made from any appropriate material while those with a diameter less than 3.0 FR are preferably made from metal for structural strength and ease of manufacturing.

An exemplary method of use of the stents shown in FIGS. 18–22 is described as follows. In this exemplary method, the stent is used to remove one or more stone obstructions from the ureter. One skilled in the art will appreciate, however, that the stents described herein are not limited to ureteral use. Use in other passageways is possible, as described in detail below. The stent, in a contracted state, is guided through a ureter in a retrograde manner. This may be accomplished by using a guidewire (as described above), by guiding the device directly or by other common means of device or catheter guidance. Once the device is in a desired location in the ureter, it is induced to take an expanded state or a restraining force is removed allowing it to assume an expanded state, as described above. The natural expansion of the ureter combined with the exposed void spaces 104, 104', 104" in the device facilitate the migration of an occluding object or substance, hereinafter referred to as an "occlusion," into a void space. When it is determined that a target occlusion (such as a stone) has lodged in the void space of the cage, the device can be induced to take a contracted state or pulled from the ureter, thereby contracting the cages around the target occlusion. The contracted state acts to compress and/or enclose the occlusion within the smooth body, facilitating removal. The device is then removed from the ureter along with the "captured" occlusion. Similarly, occlusions may become trapped between adjacent cages. In this instance, the occlusion is "swept" or "dragged" out of the ureter between the open cages. It will be understood by those skilled in the art that intermediate steps may be employed in combination with those set forth here to facilitate removal of the occlusion. For example, adding a step of using a laser or other application to break up the occlusion into smaller pieces may be employed. Many of the "traditional" techniques may be used in combination with the present invention as aids in the removal of the occlusion. Further, the device of the invention may be used to only expand the ureter, when such a procedure is desired.

Figure 23A:
FIG. 23A is a perspective view of an obstruction within a passageway.

In accordance with another exemplary embodiment, a method for capturing an obstruction within a passageway is described in FIGS. 23A–23E. FIG. 23A illustrates an obstruction 120 within a passageway 114. The passageway may be, for example, a body passage such as a ureter or a duct within the pancreaticobiliary system such as a hepatic duct, cystic duct, common bile duct, or pancreatic duct. Additional exemplary body passages include an esophagus, a blood vessel, an airway such as a trachea, a urethra, a fallopian tube, or a bowel passage such as a colon or small bowel. Alternatively, the passageway could be tubing temporarily implanted in a subject that exits the body, such as external drainage tubing, a feeding tube, an intravenous tube, or a chest tube. The term subject will be understood to include human and non-human animals. Subject may also include any material used as the subject of the methods described herein, including, for example, tissues, organs, plants, etc. The obstruction may be any matter that occludes, either partially or fully, a passageway such as those noted above. Such matter may be solid in form, such as stones, or may be more fluid, such as biosludge, fibrin clots, or formed clots, which may still be sufficient to occlude a passageway. By way of specific example, the passageway 114 of FIG. 23A could be a ureter and the obstruction 120 could be a kidney stone lodged within the ureter.

Figure 23B:
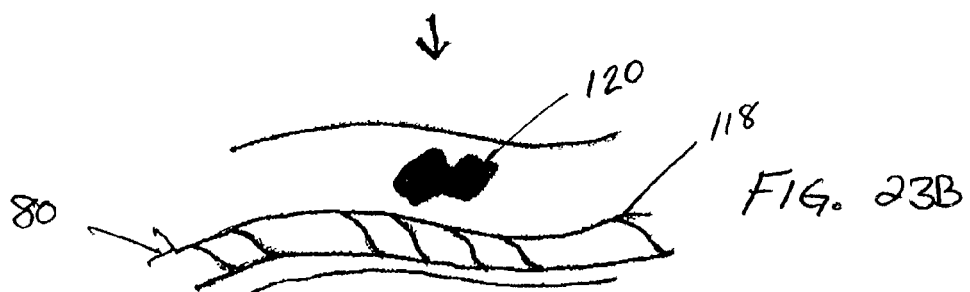
FIG. 23B is a perspective view of the stent of FIG. 21 being inserted into the passageway.

In the following description of an exemplary method of capturing an obstruction, a stent 80, as described above in connection with FIGS. 21–22, is utilized to capture the obstruction. One skilled in the art will appreciate that other stent or obstruction removal devices could also be used to accomplished the described exemplary method. As illustrated in FIG. 23B, the stent 80, as also shown in FIG. 21, may be guided through the passageway 114 while the stent is in a contracted state. As pictured in FIG. 23B, the distal end 118 of the stent 80 has been advanced beyond the obstruction 120 by partially dilating the passageway alongside the obstruction or maneuvering around the obstruction in a similar manner. This guided placement can be accomplished as described in FIGS. 12–14 by using a guidewire 78 and pusher 82 to deliver the stent 80 to the desired location. Alternatively, a sleeve can be used to deliver the stent to the desired location by providing the necessary rigidity and force in the distal direction. Any of the described insertion methods can also be performed in conjunction with an endoscope to provide visualization of the passageway and obstruction. The endoscope can be used before advancing the stent and insertion tools or in conjunction with advancing the stent and insertion tools by utilizing an endoscope with a working channel.

Figure 23C:
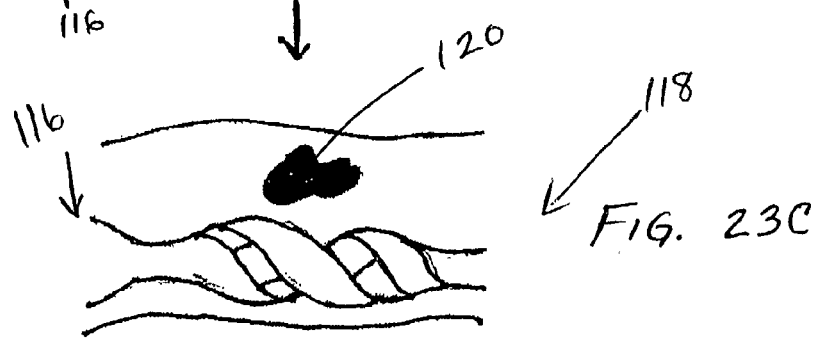
FIG. 23C is a perspective view of the stent of FIG. 21 in a partially expanded state.
Figure 23D:
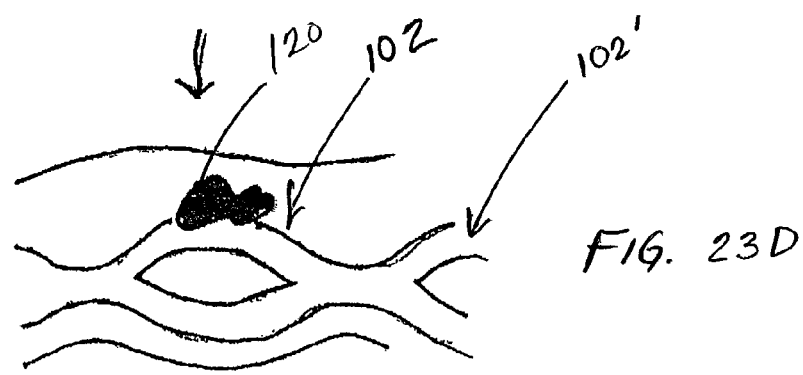
FIG. 23D is a perspective view of the stent of FIG. 22 before the obstruction has been captured within one of the cages.
Figure 23E:
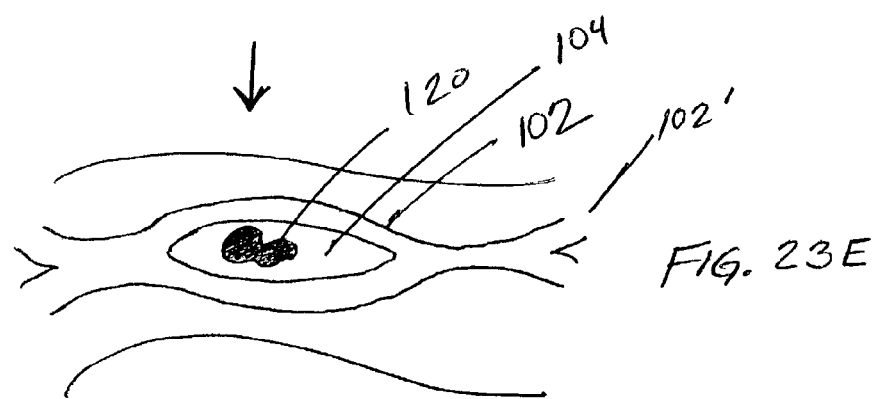
FIG. 23E is a perspective view of the stent of FIG. 22 after the obstruction has been captured within one of the cages.

As demonstrated in FIGS. 23C–23D, once the stent reaches the desired location, the stent is twisted from the proximal end 116 in order to expand the stent and create three-dimensional cages 102, 102', thereby taking the expanded shape shown in FIG. 22. This twisting may be accomplished while the distal end 118 of the stent 80 is anchored within the passageway or while the distal end is not anchored. If the distal end is not anchored, the frictional force of the passageway against the external surface of the stent may provide sufficient purchase to allow the stent to be expanded by twisting. Alternatively, barbs or other features that lock the distal end of the stent to prevent movement may be included. Either during expansion or after full expansion, the stent may capture an obstruction 120 within one or more of the three-dimensional cages 102, 102' as illustrated in FIG. 23E. The obstruction may enter the cage though a void space 104 during expansion or the user may rotate the expanded stent or move the expanded stent axially in order to coax the obstruction through a void space and into the cage. Alternatively, obstructions may become trapped between adjacent cages.

When it is determined that the target obstruction has lodged within a cage, the stent may then be rotated in the direction opposite the original twisting to once again contract the stent and enclose the captured obstruction within the stent body. Upon contraction, the stent will once again take a reduced diameter state as shown in FIG. 21 and have a smooth external surface that facilitates removal. Alternatively, after capturing the target obstruction, the stent may simply be pulled from the proximal end which will also contract the stent and facilitate removal of the stent and captured obstruction. The stent may also be pulled from the proximal end to displace the captured obstruction to a location within the passageway more suitable for treating the obstruction utilizing techniques such as extracorporeal lithotripsy, laser lithotripsy, or mechanical means. This proximal pulling technique is a preferred method for extracting or displacing obstructions trapped between adjacent cages.

In accordance with another exemplary embodiment, a method of use of the stent shown in FIGS. 21–22 includes guiding and expanding the stent as described above, however, when it is verified that one or more target obstructions have been captured within one or more cages, the stent is then rotated in a direction consistent with the original twisting to move the obstruction through the stent in a distal to proximal direction. This rotation and associated movement of the obstruction is accomplished through a corkscrew action of the helical pattern stent. The rotation can continue until the obstruction exits the proximal end of the stent or only until the obstruction reaches a location in the passageway that is more suitable for removal of the stent with the captured obstruction remaining inside. Alternatively, the rotation can continue until the obstruction is moved to a location within the passageway more suitable for treating the obstruction utilizing techniques such as extracorporeal lithotripsy, laser lithotripsy, or mechanical means.

In accordance with another exemplary embodiment similar to that described immediately above, a method of use of the stent described in FIGS. 21–22 includes similar guidance and expansion methodology, however, this method includes trapping one or more obstructions between adjacent cages on the external surface of the stent. Once it is verified that an obstruction is trapped between adjacent cages and the inner surface of the passageway, the stent is rotated in a direction consistent with the original twisting to move the obstruction along the external surface of the stent in a distal to proximal direction. This rotation and associated movement is accomplished through a corkscrew action of the helical pattern stent similar to the corkscrew action described above. This rotation can continue until the obstruction reaches the end of the stent or only until the obstruction reaches a location in the passageway more suitable for subsequent treatment, examples of which are described above.

Figure 24A:
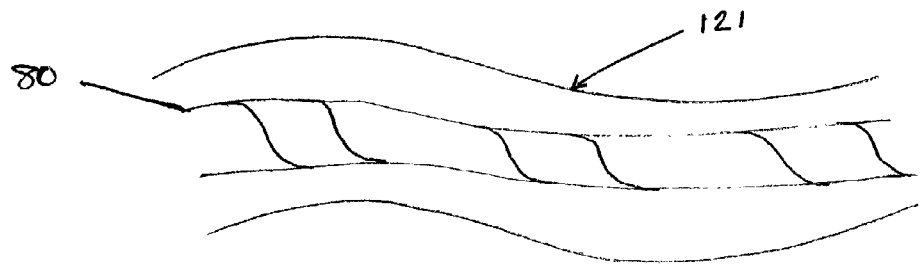
FIGS. 24A–24D illustrate a method for obtaining a tissue sample from an inner surface of a body passage utilizing a stent.
Figure 24B:
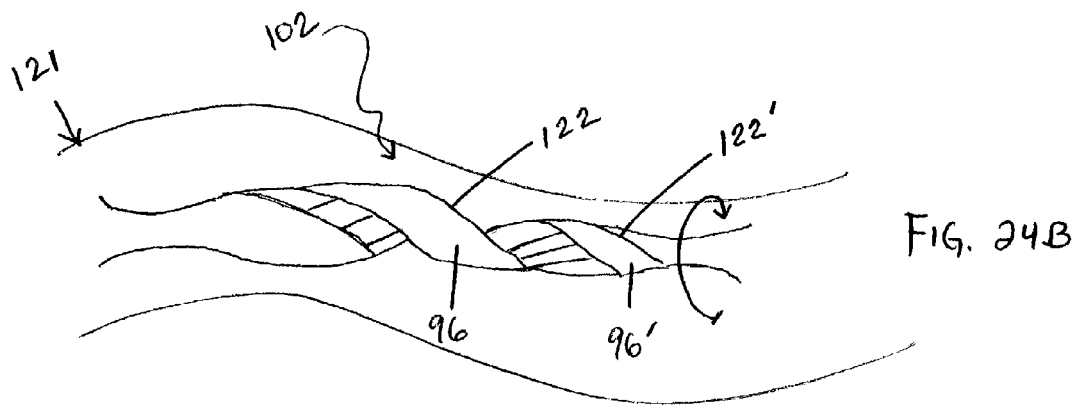
Figure 24C:
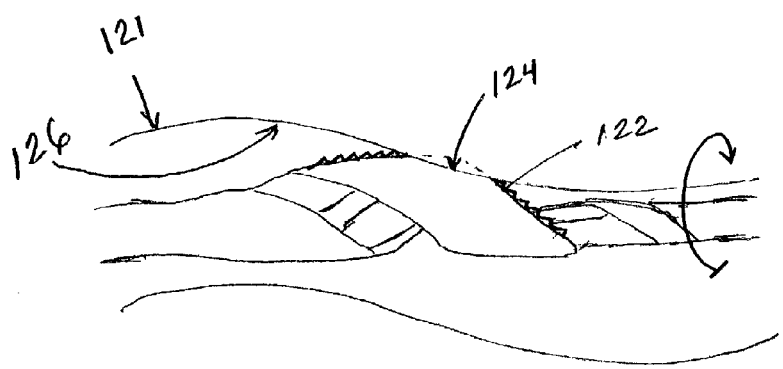
Figure 24D:
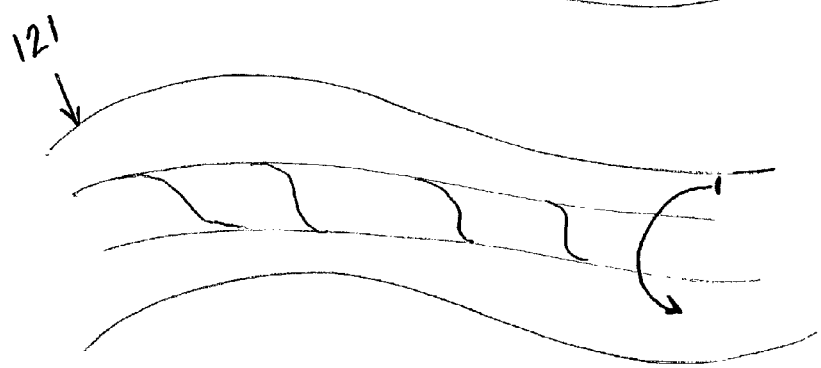

In accordance with another exemplary embodiment, FIGS. 24A–24D describe a method of use of the stent illustrated in FIGS. 21–22 for obtaining tissue samples from a body passage. This method includes guiding a stent 80 in the contracted state as described in FIG. 21 into a body passage 121 as shown in FIG. 24A. The stent used for this method includes flexible elongate members with abrading edges. As illustrated in FIG. 24B, once the stent has reached the desired location within the body passage, the stent is twisted to expand the flexible elongate members 96, 96' and create one or more cages 102, each with a leading abrading edge 122. During twisting and once expanded, as shown in FIG. 24C, the stent can be rotated in the same direction as the original twisting to scrape tissue samples 124 from the inner surface of the body passage 126 utilizing the abrading leading edge 122 of one or more of the cages. Once tissue samples have been obtained, the stent may be rotated in the opposite direction to contract the stent and capture the tissue samples within the cages as shown in FIG. 24D, prior to removing the device from the body passage.

The method for obtaining tissue samples described above can be used in performing biopsies in different body passages, including but not limited to bowel passages such as the colon and small bowel, or pancreaticobiliary ducts such as the hepatic duct, cystic duct, common bile duct, or pancreatic duct. Additional appropriate body passages may include the ureter, urethera, fallopian tubes, blood vessels, esophagus, trachea, or breast ducts. The abrading edges 122, 122' of the flexible elongate members 96, 96' can be achieved by manufacturing the stent from a semi-rigid plastic such as polyethylene capable of maintaining sufficient rigidity in order to effectively scrape tissue samples while having sufficient flexibility to be able to negotiate body passages upon insertion and removal. Alternatively, the abrading edges can be achieved by honing the edges of the flexible elongate members to facilitate tissue scraping. Similarly, the abrading edges may be made by attaching metal inserts to the edges of the flexible elongate members to achieve the requisite tissue scraping capacity. Also, the edges may be made abrading by scoring the edges of the flexible elongate members, serrating the edges, or shaping the edges into abrading patterns such as small brushes, combs, or curved teeth.

The devices described in FIGS. 18–22 may be made in the following manner. A device body 88 made of a flexible tube 90 is either formed with apertures 98, 98', 98" along its length or the apertures are cut into the flexible tube. These apertures define the edges of the flexible elongate members 96, 96', 96". The apertures may be of very small width, having zero tolerance, or may be expanded to form wider slots as seen in FIG. 9. It will be understood that the apertures may be formed longitudinally, non-longitudinally or in any other arrangement in accordance with the invention. Further, in one embodiment, the device is maintained in an expanded state while heat is applied to induce a shape memory effect in a material of the device. For example, if the device is constructed of silicone, it is heated to a high temperature, but below the melting point of the polymer, and then allowed to cool. Upon cooling, the device will hold the expanded state when at rest. Additionally, a sheath or adhesive can then be applied to hold the device in a contracted state until use.

An alternative method for making the devices described in FIGS. 21–22 is described in FIGS. 25A–25E. A device body 88 made of a flexible tube 90 is secured at one end and then twisted to induce a helical or spiral shape as shown in FIGS. 25A–25B. Once twisted as shown in FIG. 25C, longitudinal apertures 98, 98', 98", 100, 100', 100", 101, 101', 101" are cut into the flexible tube utilizing a cutting tool 126 as demonstrated in 25D. The cutting tool may be any tool capable of penetrating the tubular body such as a knife, razor, or waterjet. The apertures may be of very small width, having zero tolerance, or may be expanded to form wider slots as seen in FIG. 9. After creating the longitudinal apertures 98, 98', 98", 100, 100', 100", 101, 101', 101", the flexible tube is released to yield a flexible tubular body with helical apertures defining multiple flexible members arranged in a helical pattern as illustrated in FIG. 25E.

Another alternative method for making the devices described in FIGS. 21–22 may include cutting helical apertures in a flexible tubular body by moving a cutting tool about the longitudinal axis of the tubular body in a helical pattern. This may be accomplished by moving the cutting tool about a stationary tubular body in a helical pattern, by moving the tubular body about a stationary cutting tool in a helical pattern, or by a combination of these two methods.

Subsequently, the stent may be heated to a temperature sufficient to induce a shape memory in the material of the stent in order to bias the stent towards that shape. This heating can be done while the stent is in a contracted state, when the flexible members are partially expanded, or when the flexible members are fully expanded.

It will be appreciated by persons skilled in the art that the present invention is not limited to what has been particularly shown and described herein above, and that the drawings are not to scale. A variety of modifications and variations are possible in light of the above teachings without departing from the scope and spirit of the invention, which is limited only by the following claims.

The invention claimed is:

1. A device for capturing an obstruction within a passageway, the device comprising:
  a flexible tubular body having:
    a proximal end;
    a distal end; and
    at least two expandable portions separated from each other along the length of the body;
  wherein each of the at least two expandable portions of the tubular body comprises a plurality of flexible elongate members defined by a plurality of slits cut in the wall of the tubular body that are helically oriented relative to a longitudinal axis of the tubular body such that, when the tubular body is in a contracted state, adjacent ones of the flexible elongate members so touch that the tubular body forms an internal lumen and a smooth exterior surface, the flexible elongate members being expandable to form a cage when the expandable portion is expanded to an increased diameter state, in which adjacent members are so spaced apart as to form apertures through which the obstruction can enter the cage, the cage being generally centered about the longitudinal axis of the tubular body between the proximal end and the distal end, and flanked on either side along the longitudinal axis by unslitted portions of the flexible tubular body;
  wherein the at least two expandable portions are separated by a first unslitted portion, so that the tubular body has at least three unslitted portions alternating with at least two expandable portions along the longitudinal axis of the tubular body; and
  wherein the flexible tubular body is formed from a material so flexible that twisting the tubular body in a first direction transitions the tubular body to the expanded state, and twisting the tubular body in a second direction opposite to the first direction transitions the tubular body to the contracted state.

2. The device of claim 1, wherein the flexible tubular body is made of a polymer.

3. The device of claim 2, wherein the polymer is reinforced with fibers.

4. The device of claim 2, wherein the polymer comprises polyurethane.

5. The device of claim 1, wherein the plurality of flexible elongate members are helically oriented at a ±45° angle relative to the longitudinal axis of the tubular body.

6. The device of claim 1, wherein the plurality of flexible elongate members are helically oriented at an angle greater than 0° but less than 90° relative to the longitudinal axis of the tubular body.

7. The device of claim 1, wherein the tubular body comprises two or more flexible elongate members that are expandable to form a three-dimensional cage.

8. The device of claim 1, wherein the tubular body comprises three or more flexible elongate members that are expandable to form a three-dimensional cage.

9. The device of claim 1, wherein the device is configured for insertion into a body passage.

10. The device of claim 9, wherein the device is made of a bioabsorbable material.

11. The device of claim 9, wherein the device is coated or impregnated with an anti-inflammatory substance.

12. The device of claim 9, wherein the device is coated or impregnated with a substance capable of treating an obstruction.

13. The device of claim 9, wherein the device is coated or impregnated with a topical anesthetic substance.

14. The device of claim 9, wherein the device has an outer diameter of approximately 7.0 FR (0.092") to facilitate insertion into a ureter.

15. The device of claim 9, wherein the device has an outer diameter of approximately 1.0 FR (0.0125") to facilitate insertion into a breast duct.

16. The device of claim 9, wherein the device has an outer diameter between 3.0 FR (0.039") and 7.0 FR (0.092") to facilitate insertion into a pancreaticobiliary duct.

17. The device of claim 9, wherein the device has an outer diameter of approximately 14.0 FR (0.184") to facilitate insertion into a fallopian tube.

18. The device of claim 9, wherein the device has an outer diameter of approximately 18 mm (0.71") to facilitate insertion into an esophagus.

19. The device of claim 9, wherein the device has an outer diameter between 25 mm (1.0") and 35 mm (1.4") to facilitate insertion into a colon.

20. The device of claim 1, wherein the device is made of silicone.

21. The device of claim 1, wherein the device is coated or impregnated with an antimicrobial substance.

22. The device of claim 1, wherein the cage is marked with a marking substance to allow in vivo visualization.

23. The device of claim 22, wherein the marking substance is radiopaque.

24. The device of claim 22, wherein the marking substance is non-ferromagnetic in order to be visualized using magnetic resonance imaging.

25. The device of claim 1, wherein at least one flexible elongate member has an abrading edge.

26. The device of claim 25, wherein the abrading edge comprises a metal insert attached to the flexible member.

27. The device of claim 25, wherein the abrading edge comprises a honed edge of the flexible elongate member.

28. The device of claim 25, wherein the abrading edge comprises a serrated edge of the flexible elongate member.

29. The device of claim 25, wherein the abrading edge comprises a scored edge of the flexible elongate member.

30. The device of claim 25, wherein the abrading edge comprises brushes.

31. The device of claim 25, wherein the abrading edge comprises teeth.

32. The device of claim 1, wherein the device is configured for insertion into tubing connected to a subject.

33. The device of claim 1, wherein the device is treated with a surface coating.

34. The device of claim 33, wherein the surface coating is a hydrophilic coating.

35. The device of claim 33, wherein the surface coating is a vacuum-deposited polymer coating.

36. The device of claim 35, wherein the vacuum-deposited polymer coating comprises Parylene.

37. The device of claim 35, wherein the vacuum-deposited polymer coating comprises PTFE.

38. The device of claim 33, wherein the surface coating comprises a lubricious coating.

39. The device of claim 38, wherein the lubricious coating comprises a gel.

40. The device of claim 38, wherein the lubricious coating comprises silicone.

41. The device of claim 1, further comprising a pusher sized and shaped to press longitudinally against an end of the tubular body.

42. A method for capturing an obstruction within a passageway, the method comprising:
    (a) guiding the device of claim 1 through the passageway;
    (b) twisting the device in the first direction to expand the flexible elongate members and create at least one cage; and
    (c) capturing an obstruction within the cage.

43. The method of claim 42, wherein an endoscope is used to facilitate insertion of the device into the passageway.

44. The method of claim 42, wherein the device is inserted using a guidewire.

45. The method of claim 42, wherein the device is inserted using a sleeve.

46. The method of claim 42, further comprising extracting the obstruction by removing the device from the passageway.

47. The method of claim 42, further comprising displacing the obstruction within the passageway.

48. The method of claim 47, further comprising treating the displaced obstruction within the passageway.

49. The method of claim 42, further comprising twisting the device in the second direction to contract the device prior to removing the device from the passageway.

50. The method of claim 42, wherein the plurality of flexible elongate members are oriented at a ±45° angle relative to the longitudinal axis of the tubular body.

51. The method of claim 42, wherein the cage is defined by three or more flexible elongate members.

52. The method of claim 42, wherein the passageway comprises a body passage.

53. The method of claim 52, wherein the body passage comprises a ureter.

54. The method of claim 53, wherein the device is guided in a retrograde manner through the ureter.

55. The method of claim 53, wherein the device is guided in an anterograde manner through the ureter.

56. The method of claim 52, wherein the body passage comprises at least one of a pancreaticobiliary duct, an esophagus, a blood vessel, an airway, a urethra, a fallopian tube, a breast duct, and a bowel passage.

57. The method of claim 42, wherein the passageway comprises tubing connected to a subject.

58. The method of claim 57, wherein the tubing comprises at least one of an external drainage tube, a feeding tube, an intravenous tube, and a chest tube.

59. The method of claim 42, further comprising anchoring a distal end of the device within the passageway.

60. The method of claim 59, further comprising anchoring the distal end of the device before twisting.

61. The method of claim 59, further comprising unanchoring the device releasing the anchor before removing the device from the passageway.

62. A method for capturing an obstruction within a passageway, the method comprising:
(a) guiding the device of claim 1 through the passageway;
(b) twisting the device in the first direction to expand the flexible elongate members and create a plurality of cages; and
(c) capturing an obstruction with two or more cages.

63. The method of claim 62, wherein the obstruction is captured within two or more cages.

64. The method of claim 62, wherein the obstruction is captured between two or more cages.

65. A method for capturing an obstruction within a passageway, the method comprising:
(a) guiding the device of claim 1 through the passageway;
(b) twisting the device in the first direction to expand the flexible elongate members and create at least one cage;
(c) capturing an obstruction within one or more of the cages; and
(d) rotating the device in the first direction to displace the obstruction through the device in a direction away from a distal end of the device.

66. The method of claim 65, further comprising rotating the device until the obstruction exits the device.

67. The method of claim 65, further comprising treating the displaced obstruction within the passageway.

68. The method of claim 65, wherein the passageway comprises a body passage.

69. The method of claim 68, wherein the body passage comprises a ureter.

70. The method of claim 69, wherein the device is guided in a retrograde manner through the ureter.

71. The method of claim 69, wherein the device is guided in an anterograde manner through the ureter.

72. The method of claim 68, wherein the body passage comprises at least one of a pancreaticobiliary duct, an esophagus, a blood vessel, an airway, a urethra, a fallopian tube, a breast duct, and a bowel passage.

73. The method of claim 65, wherein the passageway comprises tubing connected to a subject.

74. The method of claim 73, wherein the tubing comprises at least one of an external drainage tube, a feeding tube, an intravenous tube, and a chest tube.

75. A method for capturing an obstruction within a passageway, the method comprising:
(a) guiding the device of claim 1 through the passageway;
(b) twisting the device in the first direction to expand the flexible elongate members and create a plurality of cages;
(c) capturing an obstruction with two or more cages; and
(d) rotating the device in the first direction to displace the obstructions through the device in a direction away from a distal end of the device.

76. The method of claim 75, wherein the obstruction is captured within two or more cages.

77. The method of claim 75, wherein the obstruction is captured between two or more cages.

78. A method for making the device of claim 1, the method comprising:
(a) securing an end of a flexible tubular body;
(b) twisting the flexible tubular body about a longitudinal axis of the body;
(c) creating a plurality of longitudinal apertures in a body wall of the twisted tubular body, the apertures penetrating a cross-section of the body wall and defining flexible elongate members in the body wall; and
(d) releasing the twisted tubular body.

79. The method of claim 78, further comprising sharpening an edge of at least one flexible elongate member by honing the edge.

80. The method of claim 78, further comprising sharpening an edge of at least one flexible elongate member by attaching a metal insert to the edge.

81. The method of claim 78, wherein the apertures are circumferentially spaced about the body wall.

82. The method of claim 78, further comprising heating the device to a temperature sufficient to induce a shape memory of the untwisted state.

83. The method of claim 78, further comprising:
(a) expanding the flexible elongate members to a partially expanded state; and
(b) heating the device to a temperature sufficient to induce a shape memory of the partially expanded state.

84. The method of claim 78, further comprising:
(a) expanding the flexible elongate members to a fully expanded state; and
(b) heating the device to a temperature sufficient to induce a shape memory of the fully expanded state.

85. A method for obtaining tissue samples from a body passage, the method comprising:
(a) guiding the device of claim 1 through a body passage, wherein at least one of the flexible elongate members has an abrading edge;
(b) twisting the device in the first direction to expand the flexible elongate members and create at least one cage;
(c) rotating the device to bring the abrading edge into contact with an inner surface of the body passage and to scrape a tissue sample from the inner surface of the body passage;
(d) twisting the device in the second direction to contract the device and capture the tissue sample within the cage; and
(e) removing the device from the body passage.

86. The method of claim 85, wherein an endoscope is used to facilitate insertion of the device into the passageway.

87. The method of claim 85, wherein the device is inserted using a guidewire.

88. The method of claim 85, wherein the device is inserted using a sleeve.

89. The method of claim 85, wherein the body passage comprises at least one of a pancreaticobiliary duct, an esophagus, a blood vessel, an airway, a ureter, a urethra, a fallopian tube, a breast duct, and a bowel passage.

90. A method for obtaining tissue samples from a body passage, the method comprising:
(a) guiding the device of claim 1 through a body passage, wherein a plurality of the flexible elongate members have abrading edges;
(b) twisting the device in the first direction to expand the flexible elongate members and create a plurality of cages;
(c) rotating the device to bring the abrading edges into contact with an inner surface of the body passage and to scrape tissue samples from multiple locations on the inner surface of the body passage;
(d) twisting the device in the second direction to contract the device and capture the tissue samples within the cages; and
(e) removing the device from the body passage.

* * * * *